United States Patent

Denarie et al.

[11] Patent Number: 5,986,092
[45] Date of Patent: Nov. 16, 1999

[54] PROCESS FOR THE PREPARATION OF N-SUBSTITUTED LACTAMS

[75] Inventors: Michel Denarie, Pernes les Fontaines; Khann Ly Kok, Avignon, both of France

[73] Assignee: SNPE, Paris, France

[21] Appl. No.: 08/888,492

[22] Filed: Jul. 8, 1997

[30] Foreign Application Priority Data

Jul. 31, 1996 [FR] France .................................. 96 09631

[51] Int. Cl.$^6$ ...................... C07D 211/74; C07D 223/10; C07D 227/08; C07D 41/06
[52] U.S. Cl. .......................... 540/451; 540/533; 546/243; 548/952; 548/543
[58] Field of Search .................................. 548/952, 543; 546/243; 540/533, 451

[56] References Cited

U.S. PATENT DOCUMENTS

| | | | |
|---|---|---|---|
| 3,865,814 | 2/1975 | Heinz et al. | 260/239.3 |
| 4,692,523 | 9/1987 | Schorr et al. | 540/533 |
| 4,812,566 | 3/1989 | Toshinari | 540/533 |
| 4,973,688 | 11/1990 | Lingchong et al. | 540/533 |
| 5,276,165 | 1/1994 | Weyer et al. | 548/554 |

FOREIGN PATENT DOCUMENTS

| | | |
|---|---|---|
| 0218976 | 4/1987 | European Pat. Off. . |
| 9614299 | 5/1996 | WIPO . |

OTHER PUBLICATIONS

Yang et al., Huaxue Shiji (1993), 15 (2), 81–82. (Abstract only), 1993.

Du et al., Jinan Daxue Xuebao, Ziran Kexue Yu Yixueban (1992), 13 (1), 47–50. (Abstract only), 1992.

Yang et al., Zhongguo Yiyao Gongye Zazhi (1992), 23 (5), 195–7, 207. (Abstract only), 1992.

Heterocycles, vol. 12, No. 11, 1979, pp. 1449–1451, XP000646488.

*Primary Examiner*—Mukund J. Shah
*Assistant Examiner*—Bruck Kifle
*Attorney, Agent, or Firm*—Bucknam and Archer

[57] ABSTRACT

The invention relates to a process for the preparation of N-substituted lactams by reaction of a lactam, which is unsubstituted on the nitrogen, with an organic halide in the presence of at least one solid-liquid phase transfer catalyst, such as a quaternary ammonium salt, and of at least one solid inorganic base, such as an alkali metal hydroxide, and in the absence of solvent. By this process, N-substituted lactams are obtained with good yields and high purity. The absence of solvent makes possible a considerable gain in productivity and an improvement in safety and in regard for the environment.

18 Claims, No Drawings

PROCESS FOR THE PREPARATION OF N-SUBSTITUTED LACTAMS

FIELD OF THE INVENTION

The object of the invention is an improved process for the preparation of N-substituted lactams and the invention more particularly relates to a more economical and more reliable process for the preparation of N-substituted lactams by reaction of lactams, which are unsubstituted on the nitrogen, with an organic halide.

BACKGROUND OF THE PRIOR ART

N-Substituted lactams can be prepared, according to a standard process, by reaction of the alkali metal salts of lactams with alkylating agents, for example as described in U.S. Pat. No. 4,122,170. The alkali metal salts used as starting compounds have to be prepared beforehand by reaction of alkali metals or alkali metal hydrides with the corresponding lactams, in the presence of an inert solvent and under a nitrogen atmosphere. This process is not economical due to the high cost of alkali metals or alkali metal hydrides and the large amounts of solvent which are required.

Another process has been disclosed by G. L. Isele et al. (Synthesis, 1971, 266), which consists of alkylating caprolactam with an alkyl bromide or chloride in the presence of dimethyl sulphoxide as solvent and of potassium hydroxide as acceptor of hydrohalic acid. The advantageous results of this process would be due to the action of the solvent, which would promote the formation of the potassium salt of the lactam. However, this process is not economical on an industrial scale. Potassium hydroxide is relatively expensive. The not very common solvent is expensive and used in large amounts. The separation of the product obtained and the dimethyl sulphoxide can, moreover, present problems when the boiling points of these compounds are similar.

According to the process described in U.S. Pat. No. 3,865,814, lactams are reacted with an alkyl or aralkyl halide in the presence of an alkali metal hydroxide and in the absence of solvent but a solvent is nevertheless used in all the examples in order to recover the portion of N-substituted lactams contained in the salt formed, which salt is separated by filtration. Moreover, due to the high exothermicity of the reaction, it is indicated that it is preferable, in carrying out the process, to add the alkali metal hydroxide to the mixture of lactam and halogenated organic compound and/or to add an inert solvent with an appropriate boiling point. Large amounts of by-products, such as ethers, are formed. Fractional distillations are then required in order to recover the N-substituted lactams and the latter are still contaminated by a significant amount of unreacted lactams. The yields are low. This process is consequently not suited to industry either. The N-substituted lactams are insufficiently pure and the heat given off by the reaction is difficult to control on an industrial scale.

More recently, processes for the preparation of 1-dodecylazacycloheptan-2-one are described, in U.S. Pat. No. 4,812,566 and U.S. Pat. No. 4,973,688, in which a phase transfer catalyst and organic hydrocarbon solvents, such as benzene, toluene, xylene, cyclohexane, n-hexane and petroleum ether, are used. It is necessary to use amounts of solvents such as from 1 to 3 times the total weight of the reactants. These solvents are inflammable and, more- over, some are toxic, such as benzene and toluene. The storage, the recycling and the removal of these solvents require many operations in order to have regard for safety and the environment, which significantly increases the cost of the process.

SUMMARY OF THE INVENTION

The object of the invention is a process which does not exhibit the disadvantages of the prior processes, which is much more economical and more reliable and which is consequently entirely suitable for industrial use.

According to the process of the invention, N-substituted lactams are prepared by reaction of a lactam, which is unsubstituted on the nitrogen, with an organic halide in the presence of at least one solid-liquid phase transfer catalyst and of at least one solid inorganic base and in the absence of solvent.

The expression an organic halide denotes a halogenated hydrocarbon derivative.

The absence of solvent in the process according to the invention makes possible, both during the reaction itself and during the stages of isolation of the N-substituted lactams, a considerable gain in productivity and an improvement in the safety of the process and in regard for the environment. The problems of storing and recycling the solvents and those of removing the waste resulting from the recycling are thus avoided. The N-substituted lactams are obtained with good yields and with very few troublesome by-products.

Although the reaction according to the invention generates water and without it being necessary to remove it, the process is preferably carried out while limiting the presence of water in the reaction mixture as much as possible. Use is consequently made of the form of the compounds which contains the least water, they are optionally dried and the entry of water into the reactor is avoided.

The lactams used as starting compounds are the compounds represented by the general formula:

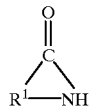

in which $R^1$ represents an aliphatic hydrocarbon chain containing from 2 to 11, preferably from 3 to 7, carbon atoms, which chain is unsubstituted or substituted by one or more linear or branched alkyl groups each having from 1 to 4 carbon atoms.

A single lactam or a mixture of lactams can be used.

Mention may be made, as examples of lactams, of pyrrolidone, piperidone, caprolactam, γ-tert-butylcaprolactam, the mixture of β,β, δ- and β,δ,δ-trimethylcaprolactams, heptanelactam, octanelactam, decanelactam or dodecanelactam.

The lactams are reacted with organic halides of formula:

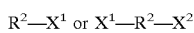

in which $X^1$ and $X^2$, which are identical or different, represent a halogen atom, such as a chlorine, bromine or iodine atom, preferably a chlorine or bromine atom, and $R^2$ represents a saturated or unsaturated, substituted or unsubstituted, mono- or divalent hydrocarbon group and preferably a substituted or unsubstituted group of formula:

in which $R^3$ represents a hydrogen atom or $R^3$ and $R'^3$ each represent a substituted or unsubstituted hydrocarbon group, which is monovalent for $R^3$ and divalent for $R'^3$, having from 1 to 17 carbon atoms, which can be formed by straight or branched aliphatic chains or alicyclic or aromatic rings in any combination and which can contain olefinic bonds, and n represents the number 0 or 1.

The substituents of the $R^2$, $R^3$ and $R'^3$ groups can be chosen from hydrocarbyloxy or hydrocarbylthio groups, such as methoxy, ethyloxy, methylthio and ethylthio groups.

Mention may be made, as examples of organic halides, of: methyl, ethyl, propyl, butyl, isobutyl, tert-butyl, allyl, methallyl, pentyl, hexyl, heptyl, octyl, cyclohexylmethyl, 3-cyclohexylpropyl, nonyl, decyl, undecyl, dodecyl, tridecyl, tetradecyl, pentadecyl, hexadecyl, heptadecyl, octadecyl, methoxyethyl, benzyl or 3-(p-methylphenyl) propyl chlorides, bromides or iodides ethylene or hexylene dichloride or dibromides, the 2-chloro- or 2-bromomethylnaphtalene.

The organic halide and the lactam can be reacted in a stoichiometric amount. An excess of the least expensive compound or of the compound which is the most easily removed during the final treatment, which is generally the lactam, is preferably used. The excess is generally between approximately 2 and approximately 5%, as molar equivalents.

The inorganic bases which can be used in the process of the invention are in particular alkali metal hydroxides, such as sodium hydroxide and potassium hydroxide, or alkaline-earth metal hydroxides, such as calcium hydroxide and magnesium hydroxide. A single base or a mixture of a number of these bases can be used. Alkali metal carbonates, such as potassium carbonate, can also be employed with one or more of these bases.

Sodium hydroxide is preferably used, for reasons of economy.

According to the process of the invention, the bases are in solid form, such as, for example, in the form of flakes, pearls, powder or other similar form, and are preferably anhydrous.

The amount of base used can be between approximately 1.2 and approximately 3 molar equivalents with respect to the reactant which is present in the lower amount and is preferably approximately 2 equivalents.

The reaction scheme of the process with a monohalogenated organic halide is as follows:

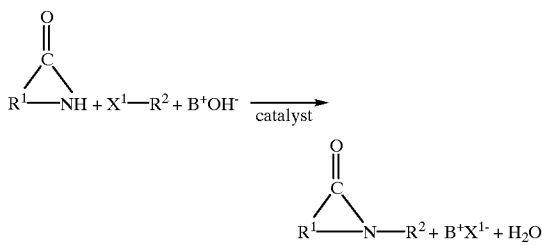

The reaction is carried out in the absence of solvent but in the presence of at least one phase transfer catalyst of solid-liquid type.

The phase transfer catalysts which can be used are the compounds which are generally known to be solid-liquid phase transfer catalysts, such as quaternary onium salts, such as ammonium, phosphonium and occasionally arsonium salts, guanidinium salts, it being possible for these onium or guanidinium salts to be attached to a support, polyethers, such as polyethylene glycols, crown ethers and cryptands. An anhydrous form of the catalyst is preferably used.

Particularly useful catalysts are the quaternary ammonium salts of formula:

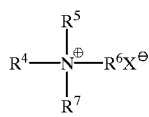

in which $R^4$, $R^5$, $R^6$ and $R^7$ are alkyl or aralkyl groups having from 1 to 18 carbon atoms, the total number of carbon atoms contained in the $R^4$ to $R^7$ groups being from 10 to 40, preferably from 16 to 40, or two or three of the $R^4$, $R^5$, $R^6$ and $R^7$ groups form part, together and with the nitrogen atom, of a saturated or unsaturated, substituted or unsubstituted, heterocyclic group, the remaining group or groups being alkyl or aralkyl groups.

Mention may be made, as examples of heterocyclic groups, of the pyridyl, picolyl, piperidino, morpholino, imidazolyl, pyrrolidinyl, pyrrolyl and pyrrolinyl groups. X is a suitable anion commonly used in these compounds. Mention may be made, as examples of anions, of the halide anions, such as Cl, Br and I, or the $SO_4$, $SO_4H$, OH and perchlorate anions. The Cl, $HSO_4$ and more particularly Br anions are preferably used.

These ammonium salts, as is known, may or may not be attached to a support.

The amount of catalyst used is generally between approximately 1 and approximately 10%, as molar equivalents, preferably between approximately 3 and approximately 5%, with respect to the reactant which is present in the lower amount, generally with respect to the halide. Nevertheless, a larger amount, if it does not prevent the mixture from being stirred, can also be used.

The catalysts which are well suited are those in which the $R^4$, $R^5$, $R^6$ and $R^7$ groups are symmetrical and which each contain at least 4 carbon atoms or those in which not more than two of these groups have less than 4 carbon atoms. Mention may be made, as examples of these catalysts, of tetrabutylammonium bromide or hydrogen-sulphate or tricaprylmethylammonium chloride. The preferred catalyst is tetrabutylammonium bromide.

The process is particularly well suited to the production of N-substituted lactams which have a melting point of less than or equal to 60° C.

It is possible first of all to mix the lactam and the halide, to heat the mixture and then to add the catalyst and subsequently the base, so that the reaction does not run away, but this operation is, however, difficult to control and the mixture often becomes very pasty or similar to a gel. The preferred implementation of the process of the invention consists of first of all suspending the base and the phase transfer catalyst in the organic halide and then gradually adding the lactam, generally molten, to the suspension maintained at the reaction temperature. By following this procedure, the mixture can surprisingly be easily stirred, is not converted into a gel and the amount of ether produced, which is an undesired impurity, is markedly lower.

In certain cases, it is possible to use a pressure higher than atmospheric pressure in order to facilitate the reaction.

The temperature of the reaction is generally between approximately 40° and approximately 120° C., preferably between 60° and 100° C.

The duration of the reaction depends on the temperature, on the amount of catalyst and on the reactants used. It is generally between approximately 1 hour and approximately 10 hours.

On completion of the reaction, the products contained in the reaction mixture are, due in particular to the absence of solvent, easily separated by conventional methods.

According to a preferred implementation, when the N-substituted lactams have no or very little solubility in water, water is added to the reaction mixture in order to dissolve the water-soluble organic and inorganic salts and the unreacted lactams. After settling and separating the aqueous phase and then, optionally, washing the organic phase and/or evaporating the residual water from the latter, crude N-substituted lactams are already obtained with a good yield and a high purity.

It is possible to purify them by a simple distillation. They are then obtained with a purity generally greater than 99%.

N-Substituted lactams have many applications. They are used, for example, as adjuvants in pesticide compositions, as pharmaceutical or cosmetic active material intermediates or solvents, or as solvent for the extraction of nuclear fission products.

The examples which follow illustrate the invention without, however, limiting it.

EXAMPLE 1

Preparation of N-octylcaprolactam.

526.4 g (3.5 mol) of octyl chloride, 280.3 g (7.0 mol) of pearl sodium hydroxide and 45.8 g (0.14 mol) of tetrabutylammonium bromide are introduced into a 2-litre jacketed reactor, equipped with a mechanical stirrer, a thermometer probe, a jacketed dropping funnel and a reflux condenser, which has been rendered inert with nitrogen. The suspension is heated to 61.5° C., with stirring, 408.3 g (3.6 mol) of molten caprolactam are slowly added over 4 hours, while maintaining the reaction mixture between 62° and 65° C., and then the stirring of the mixture is continued at this temperature for 5 hours.

The reaction mixture is then diluted with 800 g of water at a temperature of 65°–70° C. The organic layer is separated by settling. It is washed at 65°–70° C., once with an aqueous sulphuric acid solution and then with water to a constant pH. By settling and after having evaporated the residual water under reduced pressure, 758.6 g of crude N-octylcaprolactam are isolated with a purity, determined by gas chromatography (GC), of 97.8%. The chemical yield of N-octylcaprolactam is 94%.

The N-octylcaprolactam is distilled at 138°–143° C./1 mbar and a 605 g fraction of N-octylcaprolactam is recovered with a purity of 99.3% (yield: 76%).

EXAMPLES 2 and 3

Preparation of N-octylcaprolactam.

N-Octylcaprolactam (NOC) is prepared by carrying out the reaction as in Example 1, using the same molar proportion of lactam but using tetrabutylammonium bromide (TBAB) and tetrabutylammonium hydrogensulphate (TBAHS) respectively as catalysts. The conditions and the results obtained are combined in the following table:

| | EXAMPLE | |
| --- | --- | --- |
| | 2 | 3 |
| | TBAB | TBAHS |
| CATALYST | 4 mol %* | 4 mol %* |
| NaOH/Octyl chloride mol/mol | 2/1 | 2/1 |
| Reaction tem- perature | 65° C. | 65° C. |
| Composition of the crude product after reacting for 6 h, determined by GC | NOC: 94.6% Octyl chloride: 0.7% | NOC: 91.8% Octyl chloride: 3.15% |

*with respect to the octyl chloride.

COMPARATIVE EXAMPLES 1 and 2

Preparation of N-octylcaprolactam in the presence of a solvent.

N-Octylcaprolactam is prepared by using, as solvent, toluene and methyl tert-butyl ether (MTBE) respectively.

The solvent and the caprolactam are introduced into the reactor, the sodium hydroxide is added, the reaction mixture is heated and then the tetrabutylammonium bromide is added, followed gradually by the octyl chloride.

On completion of the reaction, the reaction mixture is diluted with water, is washed with an aqueous sulphuric acid solution, then with an aqueous sodium hydroxide solution and then with water and the solvent is removed by distillation under reduced pressure.

The reaction conditions and the results in comparison with those obtained in Example 1 are combined in the following Table 1.

COMPARATIVE EXAMPLES 3 to 5

Preparation of N-octylcaprolactam without catalyst and without solvent.

The same process is used as in Example 1 but without using a catalyst. The reaction temperature has to be markedly higher in order to obtain an equivalent conversion of the octyl chloride. This results in a much higher percentage of by-products in the reaction mixture.

The reaction conditions and results in comparison with those obtained according to Example 1 are combined in the following Table 2.

EXAMPLE 4

Preparation of N-dodecylcaprolactam with dodecyl bromide.

124.6 g (0.50 mol) of dodecyl bromide, 40 g (1.0 mol) of pearl sodium hydroxide and 6.44 g (0.02 mol) of tetrabutylammonium bromide are introduced into a 0.5-litre reactor equipped and treated as in Example 1. The suspension is heated to between 60° and 65° C., with stirring, 57.7 g (0.51 mol) of molten caprolactam are added slowly over 1 hour 15 min, the reaction mixture

TABLE 1

| EXAMPLE | 1 (invention) | COMPARATIVE 1 | COMPARATIVE 2 |
| --- | --- | --- | --- |
| SOLVENT | WITHOUT | TOLUENE | MTBE |
| Catalyst | TBAB | TBAB | TBAB |
| mol %/octyl chloride | 4% | 4% | 4% |
| Molar excess of caprolactam | 2.8% | 5% | 5% |
| NaOH/Octyl chloride mol/mol | 2/1 | 2/1 | 2/1 |
| Reaction temperature | 62–65° C. | 65–70° C. | 63.5° C. |
| Duration | 9 h | 8 h 30 | 20 h |
| Purity* | 97.8% | 93.5% | 96.4% |
| Residual octyl chloride* | 1% | 5.4% | 1.1% |
| Chemical yield** | 94% | 83.3% | 92.3% |

*of the crude product, determined by GC
**from GC analysis

TABLE 2

| EXAMPLE | 1 (invention) | COMPARATIVE 3 | COMPARATIVE 4 | COMPARATIVE 5 |
| --- | --- | --- | --- | --- |
| CATALYST | TBAB | | WITHOUT | |
| Reaction temperature | 62–65° C. | 77° C. | 95° C. | 123° C. |
| NaOH/octyl chloride mol/mol | 2/1 | 2/1 | 2/1 | 2/1 |
| Octyl chloride* | 1% | 21.4% | 4.6% | 1.15% |
| Octanol* | 0.2% | 0.4% | 0.5% | 3.6% |
| DOE*■ | 0.3% | 1.6% | 2.3% | 6.9% |

■ DOE: Dioctyl ether
*in the crude product after reacting for 8 h being maintained between 64° and 67° C., and then the stirring of the mixture is continued at 65° C. for 7 hours 30 min.

The reaction mixture is then diluted with 110 g of water at 65° C. The organic layer is separated by settling. It is washed, in the region of 65° C., once with an aqueous sulphuric acid solution and then with water to a constant pH. 136.5 g of a crude product are isolated by settling, the composition of which (determined by GC) is as follows:

| N-dodecylcaprolactam | 88.5% |
| --- | --- |
| dodecanol | 2.1% |
| didodecyl ether | 2.9% |
| H$_2$O | 3.9% |

The chemical yield of N-dodecylcaprolactam is 86%.

Distillation is carried out at 160°–165° C./0.7–0.5 mbar. 117.2 g of N-dodecylcaprolactam are thus recovered with a purity of 96% (yield: 80%).

EXAMPLE 5

Preparation of N-dodecylcaprolactam with dodecyl chloride.

102.4 g (0.50 mol) of dodecyl chloride, 40 g (1.0 mol) of pearl sodium hydroxide and 6.44 g (0.02 mol) of tetrabutylammonium bromide are introduced into a 0.5-litre reactor equipped and treated as in Example 1. The suspension is heated to between 60° and 65° C., with stirring, 57.7 g (0.51 mol) of molten caprolactam are added slowly over 1 hour, while maintaining the reaction mixture between 60° and 65° C., and then the stirring of the mixture is continued at this temperature for 8 hours.

The reaction mixture is then diluted with 110 g of water at 65° C. The organic layer is separated by settling. It is washed, in the region of 65° C., once with an aqueous sulphuric acid solution and then with water to a constant pH. 138.5 g of a crude product are isolated by settling, the composition of which (determined by GC) is as follows:

| N-dodecylcaprolactam | 88% |
| --- | --- |
| dodecanol | 1.1% |
| didodecyl ether | 2.6% |
| H$_2$O | 3% |

The chemical yield of N-dodecylcaprolactam is 87%.

COMPARATIVE EXAMPLE 6

Preparation of N-dodecylcaprolactam in the presence of methyl tert-butyl ether as solvent.

81 g of methyl tert-butyl ether, 17.8 g (0.157 mol) of caprolactam, 18.9 g (0.47 mol) of pearl sodium hydroxide, 2.03 g (0.006 mol) of tetrabutylammonium bromide and 37.4 g (0.15 mol) of dodecyl bromide are introduced into a 250-ml reactor equipped and treated as in Example 1.

The mixture is stirred and heated at 60° C. for 9 hours 30 min. It is then treated as in Comparative Examples 2 and 3.

34.5 g of crude N-dodecylcaprolactam are obtained with a purity of 86%.

The chemical yield of N-dodecylcaprolactam is 72%.

EXAMPLE 6

Preparation of N-octylpyrrolidone in the presence of tetrabutylammonium bromide.

538.2 g (3.6 mol) of octyl chloride, 289.6 g (7.2 mol) of pearl sodium hydroxide and 46.5 g (0.14 mol) of tetrabutylammonium bromide are introduced into a 2-litre reactor equipped and treated as in Example 1. The suspension is heated to 80° C. with stirring, 314.3 g (3.7 mol) of molten pyrrolidone are added slowly over 2 hours 30 min, the reaction mixture being maintained between 80° and 100° C., and then the stirring of the mixture is continued at 80° C. for 6 hours.

The reaction mixture is then diluted at 60° C. with 628.5 g of water. The organic layer is separated by settling. It is washed at 50°–60° C., once with an aqueous sulphuric acid solution and then with water to a constant pH. 772.5 g of a crude product are isolated by settling, the composition of which is as follows:

| | |
|---|---|
| N-octylpyrrolidone | 76% |
| octanol | 2.3% |
| dioctyl ether | 4.1% |
| H$_2$O | 12.2% |

The chemical yield of N-octylpyrrolidone is 83%.

The crude product is distilled at 122°–127° C./2–3 mbar and a 447 g fraction of N-octylpyrrolidone is thus recovered with a purity >99% containing less than 1% of dioctyl ether (yield: 63%).

EXAMPLE 7

Preparation of N-octylpyrrolidone in the presence of tricaprylmethylammonium chloride.

The preparation is carried out as in Example 6 but tricaprylmethylammonium chloride, sold under the trade name Aliquat 336, is used in place of tetrabutylammonium bromide, in the same molar proportion.

The chemical yield of N-octylpyrrolidone, determined from GC analysis of the crude product, is 62%.

COMPARATIVE EXAMPLE 7

Preparation of N-octylpyrrolidone in the presence of methyl tert-butyl ether as solvent.

81 g of methyl tert-butyl ether, 13 g (0.153 mol) of pyrrolidone, 12 g (0.3 mol) of sodium hydroxide, 1.93 g (0.006 mol) of tetrabutylammonium bromide and 23.3 g (0.149 mol) of octyl chloride are introduced into a reactor equipped and treated as in the preceding examples. The reaction mixture is heated at 80° C. for 6 hours. It is then treated as in Comparative Examples 2 and 3.

20.8 g of crude N-octylpyrrolidone are obtained with a purity of 82%.

The chemical yield of N-octylpyrrolidone is 66.7%.

COMPARATIVE EXAMPLE 8

Preparation of N-octylpyrrolidone in the absence of solvent and of catalyst.

The preparation is carried out as in Example 6 but without adding catalyst and by heating the reaction mixture for 16 hours at 100° C.

The chemical yield of N-octylpyrrolidone, determined from GC analysis of the crude product, is 12%.

EXAMPLE 8

Preparation of N-dodecylpyrrolidone.

102.4 g (0.50 mol) of dodecyl chloride, 40 g (1.0 mol) of pearl sodium hydroxide and 6.44 g (0.02 mol) of tetrabutylammonium bromide are introduced into a 0.5-litre reactor equipped and treated as in Example 1. The suspension is heated to 80° C. with stirring, 43.41 g (0.51 mol) of molten pyrrolidone are added slowly over 1 hour, the reaction mixture being maintained between 80° and 100° C., and then the stirring of the mixture is continued at 80° C. for 6 hours.

The reaction mixture is then diluted at 60° C. with 88 g of water. The organic layer is separated by settling. It is washed at 55° C., once with an aqueous sulphuric acid solution and then with water to a constant pH. 125.9 g of crude product are isolated by settling, the composition of which (determined by GC) is as follows:

| | |
|---|---|
| N-dodecylpyrrolidone | 81% |
| dodecanol | 1.55% |
| didodecyl ether | 2.80% |
| H$_2$O | 9% |

The chemical yield of N-dodecylpyrrolidone is 80%.

EXAMPLE 9

Preparation of N-benzylcaprolactam.

The preparation is carried out as in Example 1, the same proportions of reactants being used but octyl chloride being replaced by benzyl chloride. The reaction temperature is between 65° and 75° C. and the total duration of the reaction is 9 hours.

The chemical yield of N-benzylcaprolactam is 85%.

Its structure is confirmed by GC/MS (mass spectrography) coupling.

EXAMPLE 10

Preparation of N-benzylpyrrolidone.

The preparation is carried out as in Example 6, the same proportions of reactants being used but octyl chloride being replaced by benzyl chloride. The temperature of the reaction is between 75° and 85° C. and the total duration of the reaction is 8 hours 30 min.

The chemical yield of N-benzylpyrrolidone is 84%.

Its structure is confirmed by GC/MS coupling.

EXAMPLE 11

Preparation of N-(3-cyclohexylpropyl)pyrrolidone.

The preparation is carried out as in Example 6, the same proportions of reactants being used but octyl chloride being replaced by 1-chloro-3-cyclohexylpropane. The temperature of the reaction is between 75° and 85° C. and the total duration of the reaction is 8 hours 30 min.

The chemical yield of N-(3-cyclohexylpropyl)-pyrrolidone is 85%.

Its structure is confirmed by GC/MS coupling.

We claim:

1. A process for the preparation of a lactam of formula

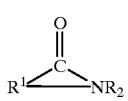

wherein R$^2$ group is a substituted or unsubstituted group of formula R$^3$CH$_2$— in which R$^3$ is a hydrogen atom or R$^3$ is unsubstituted or substituted hydrocarbon group having from 1 to 17 carbon atoms, said R³ being formed of a straight or branched aliphatic chains, alicyclic or aromatic rings in any combination and the substituents or hydrocarbyloxy or hydrocarbylthio groups, which comprises the step of reacting a lactam unsubstituted on the N atom having the formula

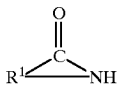

wherein R¹ is an aliphatic hydrocarbon chain containing from 2 to 11 carbon atoms, which chain is unsubstituted or substituted by at least one linear or branched alkyl group having from 1 to 4 carbon atoms, with an organic halide of formula R²—X¹ in which X¹ is a halogen atom, in the presence of at least one solid inorganic base and at least one solid-liquid phase transfer catalyst which is a member selected from the group consisting of quaternary ammonium and phosphonium salts, guanidinium salts, polyethers, crown ethers and cryptands, the amount of said catalyst being between 1 and 10% as molar equivalent, with respect to the reactant which is present in the lower amount, and in the absence of a solvent.

2. The process according to claim 1 wherein said transfer catalyst is said onium or guanidinium salt attached to a support.

3. The process according to claim 1 wherein said hydrocarbon chain R¹ contains from 3 to 7 carbon atoms.

4. The process according to claim 1 wherein said R³ contains olefinic bonds.

5. The process according to claim 1 wherein X¹ is a chlorine or bromine atom.

6. The process according to claim 1 wherein said base is an alkali metal hydroxide or an alkaline earth metal hydroxide.

7. The process according to claim 6 wherein at least one alkali metal carbonate is added to said base.

8. The process according to claim 1 wherein the base is sodium hydroxide.

9. The process according to claim 1 wherein the phase transfer catalyst is a quaternary ammonium salt of formula:

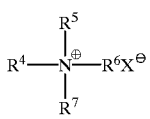

in which each of R⁴, R⁵ R⁶ and R⁷ is an alkyl or an aralkyl group having from 1 to 18 carbon atoms, the total number of carbon atoms contained in the R⁴ to R⁷ groups being from 10 to 40 or two or three of the R⁴, R⁵, R⁶ and R⁷ groups form part, together and with the nitrogen atom, of a saturated or unsaturated alkyl substituted or unsubstituted heterocyclic group, the remaining group or groups being alkyl or aralkyl groups, and X is an anion.

10. The process according to claim 9 wherein X is a halogen atom or a hydrogen sulphate group.

11. The process according to claim 8 wherein the catalyst is tetrabutylammonium bromide.

12. The process according to claim 1 wherein the process is carried out with the form of the compounds which contains the least water, to avoid the entry of water into the reaction mixture.

13. The process according to claim 1 wherein the lactam and the organic halide are reacted in a stoichiometric amount or with a slight excess of said lactam and said organic halide and the base is present in an amount of between 1.2 and 3 molar equivalents with respect to the reactant which is present in the lower amount.

14. The process according to claim 1 wherein said base and said phase transfer catalyst are first of all suspended in said organic halide and the lactam is then gradually added to the suspension maintained at the reaction temperature.

15. The process according to claim 1 wherein the reaction temperature is between approximately 40° C. and approximately 120° C.

16. The process according to claim 1 wherein on completion of the reaction, when the N-substituted lactam has no or very little solubility in water, water is added to the reaction mixture and the N-substituted lactam is recovered by settling.

17. The process according to claim 1 wherein said lactam unsubstituted on the N atom is pyrrolidone, piperidone, caprolactam, γ-tert-butylcaprolactam, the mixture of β,β,δ- and β,δ,δ-trimethylcaprolactam, heptanelactam, octanelactam, decanelactam or dodecanelactam.

18. A process for the preparation of a lactam of formula

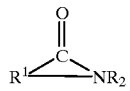

wherein R₂ is a member selected from the group consisting of alkyl or alkenyl of 1–18 carbon atoms, cyclohexylmethyl, 3-cyclohexyl-propyl, methoxyethyl, benzyl, 3-(p-methylphenyl)propyl, and methylnaphthalene and which comprises the step of reacting a lactam unsubstituted on the N atom having the formula

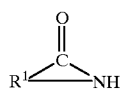

wherein R¹ is an aliphatic hydrocarbon chain containing from 2 to 11 carbon atoms, which chain is unsubstituted or substituted by one or more linear or branched alkyl groups each having from 1 to 4 carbon atoms, with an organic halide which is a chloride or a bromide of a member selected from the group consisting of an alkyl or alkenyl group of 1–18 carbon atoms, methoxyethyl, benzyl, 3-(p-methylphenyl)-propyl, and methylnapthalene and in the presence of at least one solid inorganic base and at least one solid-liquid phase transfer catalyst which is a member selected from the group consisting of quaternary ammonium and phosphonium salts, guanidinium salts, polyethers, crown ethers and cryptands, the amount of said catalyst being between 1 and 10% as molar equivalent, with respect to the reactant which is present in the lower amount, and in the absence of a solvent.

* * * * *